(12) United States Patent
Ueno

(10) Patent No.: US 6,982,283 B2
(45) Date of Patent: Jan. 3, 2006

(54) METHOD FOR TREATING DRUG-INDUCED CONSTIPATION

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 217 days.

(21) Appl. No.: 10/135,397

(22) Filed: May 1, 2002

(65) Prior Publication Data

US 2003/0073746 A1 Apr. 17, 2003

Related U.S. Application Data

(60) Provisional application No. 60/287,720, filed on May 2, 2001.

(51) Int. Cl.
*A61K 31/557* (2006.01)
*A61K 31/19* (2006.01)

(52) U.S. Cl. .................. 514/530; 514/531; 514/573
(58) Field of Classification Search ................ 514/530, 514/531, 573
See application file for complete search history.

(56) References Cited

U.S. PATENT DOCUMENTS

| | | |
|---|---|---|
| 5,073,569 A | 12/1991 | Ueno et al. |
| 5,166,174 A | 11/1992 | Ueno et al. |
| 5,212,324 A | 5/1993 | Ueno |
| 5,221,763 A | 6/1993 | Ueno et al. |
| 5,317,032 A | 5/1994 | Ueno et al. |
| 5,739,161 A | 4/1998 | Ueno |
| 6,242,485 B1 | 6/2001 | Ueno |
| 6,414,016 B1 * | 7/2002 | Ueno ............... 514/456 |
| 2003/0022933 A1 * | 1/2003 | Ueno ............... 514/506 |

OTHER PUBLICATIONS

The Merck Manual ("Constipation", Fifteenth Edition, 1987, p. 776–777.*
Harrison's Principles of Internal Medicine, 12th Edition, 1991, p. 378.*

"The management of Constipation", Prescribing Nurse Bulletin vol. 1, No. 6, 1999, pp. 21–25.*

Twycross, R.G. et al., Constipation. In: Control: "Control of Alimentary Symptoms in Far Advanced Cancer". Edinburgh: Churchill Livingstone, 1986: 166–207.

Culpepper–Morgan, J.A. et al., "Oral Naloxone Treatment of Narcotic Induced Constipation: Dose Response" NIDA Res. Monoger. 95: 399–400, 1989.

Culpepper–Morgan, J.A. et al., "Treatment of opioid–induced constipation with oral naloxone: A pilot study" Clinical Trials and Therapeutics. Clin Pharmacol Ther. 52: 90–95, 1992.

Sykes, N.P., "An investigation of the ability of oral naloxone to correct opioid–related constipation in patients with advanced cancer." Palliative Medicice. 10: 135–144, 1996.

Christmas, A. J. The Mouse Anti–Morphine Constipation Test—A Simple Laboratory Test of the Gastrointestinal Side–Effect Potential of Orally Administered Prostaglandin Analogues. Prostaglandins 18, 279–284, 1979.

Broughton, B. J. "Uterine Stimulant Action of Some ω–Chain Modified (+)–11–Deoxyprostaglandins" Prostaglandins 22, 53–64, 1981.

* cited by examiner

*Primary Examiner*—Zohreh Fay
*Assistant Examiner*—Brian-Yong Kwon
(74) *Attorney, Agent, or Firm*—Sughrue Mion, PLLC

(57) ABSTRACT

Provided is a method for treating drug-induced constipation comprising a step of administering an effective amount of a 15-keto-prostaglaindin compound to a subject suffering from drug-induced constipation or a subject having a strong possibility of suffering from it. According to the present invention, a strong antagonistic action against drug-induced constipation can be obtained without substantially losing the main effect of the drug.

12 Claims, No Drawings

METHOD FOR TREATING DRUG-INDUCED CONSTIPATION

This application claims benefit to Provisional Application No. 60/287,720 filed May 2, 2001; the disclosure of which is incorporated herein by reference.

TECHNICAL FIELD

The present invention relates to a novel use of a 15-keto-prostaglandin compound for treating drug-induced constipation.

RELATED ART

Constipation is classified into functional constipation such as an atonic constipation, spastic constipation, rectal constipation, organic constipation such as caused by bowel disease and by stenosis due to postoperative adhesion, drug-induced constipation and the like.

Drug-induced constipation occurs as a side effect caused by using a drug. The drug may cause constipation not directly but indirectly. For example, constipation may be due to hard feces caused by fluid excretion outside the body with a diuretic. Further, it may be caused by an additive or synergistic effect of using plural drugs, each of which does not introduce constipation if administrated individually.

It is known that drugs causing constipation include narcotics used for controlling cancer pain (opioid-narcotic such as morphine and codeine), anticholinergic (such as antiparkinsonism drug, tricyclic and tetracyclic antidepressant and antiincontinence drug), antacid (such as aluminium preparation), bone weight increasing agent (such as calcium preparation), diuretic, iron preparation, calcium antagonist, benzodiazepine compound, phenotiazine compound (such as chlorpromazine), $H_2$-blocker, pill, tocopherol and the like.

For example, opioid such as morphine, which is one kind of narcotics, has a depressant action on the central nervous system (such as analgesic, antitussive, sedative or hypnotic action) and, since its analgesic action is extremely strong, it is effective for almost all pains including surgical and cancer pains. On the other hand, it exhibits a constipating action by affecting gastrointestine as a peripheral effect. Accordingly, when morphine is used for treating pain, almost all the patients applied with morphine constipate, and failure to control it will cause intractable constipation. Constipation is caused by administering the dose of morphine necessary for effecting analgesic action and it is hard to become tolerant, so that constipation continues as long as the administration of morphine by any route continues. For example, if morphine is applied to a cancer patient for relieving pain without taking sufficient steps for controlling constipation, it will become unable to continue the administration of morphine, thus degrading the therapeutic result of cancer pain relief. For this reason, during repetitious administration of morphine, it is very important to control constipation.

However, it has been reported that constipation induced by opioid such as morphine is not often sufficiently controlled by conventional cathartics (Twycross, R. G. et al.: Constipation. In: Control of alimentary symptoms in far advanced cancer. Edinburgh: Churchill Livingstone, 1986: 172–177, the cited references are herein incorporated by reference).

Recently, opioid antagonist such as naloxone has been tried to relax opioid-induced constipation at the sacrifice of analgesic action of opioid. It has been reported that use of opioid antagonist against opioid-induced constipation causes side effects such as return of pain and opioid withdrawal, which is contradict to the original purpose of the opioid administration (Culpepper-Morgan, J. A. et al.: NIDA Res. Monoger. 95: 399–400, 1989. and Clin. Pharmacol. Ther. 52: 90–95, 1992: Sykes, N. P.: Palliat-Med.10:135–144, 1996, the cited references are herein incorporated by reference).

Accordingly, it has been desired to develop a drug for relaxing drug-induced constipation without losing the main effect, for example, analgesic action of opioid such as morphine, of the drug.

Prostaglandins (hereinafter, referred to as PG(s)) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

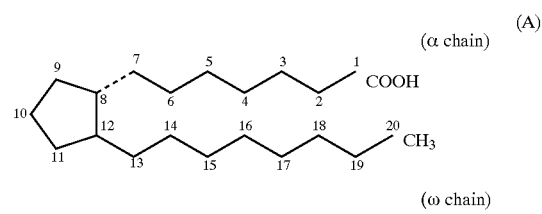

On the other hand, some of synthetic analogues of primary PGs have modified skeletons. The primary PGs are classified to PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:

Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

$PGE_1$ and $PGE_2$ and $PGE_3$ are known to have vasodilatation, hypotension, gastric secretion decreasing, intestinal tract movement enhancement, uterine contraction, diuretic, bronchodilation and anti ulcer activities. $PGF_{1\alpha}$, $PGF_{2\alpha}$ and $PGF_{3\alpha}$ have been known to have hypertension, vasoconstriction, intestinal tract movement enhancement, uterine contraction, lutein body atrophy and bronchoconstriction activities.

In addition, some 15-keto PGs (i.e. those having an oxo group at position 15 in place of the hydroxy group) and 13,14-dihydro-15-keto-PGs are known as substances naturally produced by enzymatic reactions during in vivo metabolism of primary PGs. 15-keto PG compound have been disclosed in the specification of U.S. Pat. Nos. 5,073, 569, 5,166,174, 5,221,763, 5,212,324 and 5,739,161 (These cited references are herein incorporated by reference).

The so-called primary PGs having hydroxy at the 15-position such as $PGE_1$, $PGE_2$ and the derivatives or analogs thereof are known to antagonize the enterogastric action of morphine (Christmas A. J.: Prostaglandins 18, 279–284, 1979; B. J. Broughton: Prostaglaindins 22, 53–64, 1981, the cited references are herein incorporated by reference).

However, PGE$_1$ and PGE$_2$ are well known pain enhancing substances, which augment the action of bradykinin, a strong pain producing substance, and other pain producing substances. Accordingly, the so-called primary PGs having hydroxy at the 15-position have a possibility of affecting the analgesic action of opioid.

On the other hand, a 15-keto-16-halogen-PG compound is known to be useful as a cathartic (U.S. Pat. No. 5,317,032). However, it is not known at all how the 15-keto-PG compound affects the opioid-induced constipation or how it affects the main effect of a drug, e.g., the analgesic action of opioid.

SUMMARY OF THE INVENTION

The purpose of the present invention is to provide a composition for treating drug-induced constipation, which has a strong antagonistic action against drug-induced constipation without substantially losing the main effect of the drug.

As a result of a diligent research for biological activity of 15-keto-prostaglaindin compounds, the present inventor has found that a 15-keto-prostaglaindin compound has a superior antagonistic action against drug-induced constipation. Especially, because of its superior antagonistic action against opioid-induced constipation without affecting the analgesic action of opioid such as morphine on central nervous system, the compound has been found to be very useful for controlling opioid-induced constipation. Thus, the present invention has been completed.

Namely, the present invention relates to a composition for treating drug-induced constipation comprising a 15-keto-prostaglandin compound as an active ingredient.

The present invention also relates to a method for treating drug-induced constipation comprising a step of administering an effective amount of 15-keto-prostaglaindin compound to a subject suffering from drug-induced constipation or a subject having a strong possibility of suffering from it.

The present invention further relates to use of a 15-keto-prostaglaindin compound for manufacturing a pharmaceutical composition for treating drug-induced constipation.

DETAILED DESCRIPTION OF THE INVENTION

In the present invention, the "15-keto-prostaglandin compound" (hereinafter, referred to as "15-keto-PG compound") may include any of derivatives or analogs (including substituted derivatives) of a compound having an oxo group at 15-position of the prostanoic acid skeleton instead of the hydroxy group, irrespective of the configuration of the five-membered ring, the number of double bonds, presence or absence of a substituent, or any other modification in the α or ω chain.

The nomenclature of the 15-keto-PG compounds used herein is based on the numbering system of the prostanoic acid represented in the above formula (A).

The formula (A) shows a basic skeleton of the C-20 carbon atoms, but the 15-keto-PG compounds in the present invention are not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-dehydroxy compound.

As stated above, the nomenclature of the 15-keto-PG compounds is based on the prostanoic acid skeleton. However, in case the compound has a similar partial construction as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-15-keto-PG compound. Similarly, a PG compound having 11 carbon atoms in the α-chain is named as 2-decarboxy-2-(4-carboxybutyl)-15-keto-PG compound. Further, a PG compound of which ω-chain is extended by two carbon atoms, that is, having 10 carbon atoms in the ω-chain is named as 15-keto-20-ethyl-PG compound. These compounds, however, may also be named according to the IUPAC nomenclatures.

The 15-keto-PGs used in the present invention may include any PG derivatives or analogs insofar as having an oxo group at position 15 in place of the hydroxy group. Accordingly, for example, a 15-keto-PG type 1 compound having a double bond at 13–14 position, a 15-keto-PG type 2 compound having two double bond at 13–14 and 5–6 position, a 15-keto-PG type 3 compound having three double bond at 5–6, 13–14 and 17–18 position, 13,14-dihydro-15-keto-PG compound wherein the double bond at 13–14 position is single bond.

Typical examples of the compounds used in the present invention include 15-keto-PG type 1, 15-keto-PG type 2, 15-keto-PG type 3, 13,14-dihydro-15-keto-PG type 1, 13,14-dihydro-15-keto-PG type 2, 13,14-dihydro-15-keto-PG type 3 and the derivatives or analogs thereof.

Examples of the analogs (including substituted derivatives) or derivatives include a 15-keto-PG compound of which carboxy group at the end of α-chain is esterified; a compound of which α-chain is extended; physiologically acceptable salt thereof; a compound having a double bond at 2–3 position or a triple bond at position 5–6, a compound having substituent(s) at position 3, 5, 6, 16, 17, 18, 19 and/or 20; and a compound having lower alkyl or a hydroxy (lower) alkyl group at position 9 and/or 11 in place of the hydroxy group.

According to the present invention, preferred substituents at position 3, 17, 18 and/or 19 include alkyl having 1–4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1–4 alkyl, lower alkoxy such as C1–4 alkoxy, and lower alkoxy alkyl such as C1–4 alkoxy-C1–4 alkyl. Preferred substituents at position 5 include halogen atoms such as chlorine and fluorine. Preferred substituents at position 6 include an oxo group forming a carbonyl group. Stereochemistry of PGs having hydroxy, lower alkyl or hydroxy(lower)alkyl substituent at position 9 and/or 11 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

Especially preferred compounds include a 13,14-dihydro-15-keto-PG compound which has a single bond at position 13–14; a 15-keto-16 mono or di-halogen PG compound which has one or two halogen atoms such as chlorine and fluorine at position 16; and a 15-keto-PGE compound which has an oxo group at position 9 and a hydroxyl group at position 11 of the five membered ring.

A preferred compound used in the present invention is represented by the formula (I):

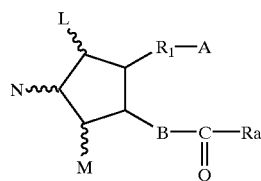

(I)

wherein
L, M and N are hydrogen, hydroxy, halogen, lower alkyl, hydroxy(lower)alkyl, or oxo, wherein at least one of L and M is a group other than hydrogen, and the five-membered ring may have at least one double bond;
A is —CH$_2$OH, —COCH$_2$OH, —COOH or a functional derivative thereof;
B is —CH$_2$—CH$_2$—, —CH=CH— or —C≡C—;
R$_1$ is a saturated or unsaturated bivalent lower or medium aliphatic hydrocarbon residue, which is unsubstituted or substituted with halogen, alkyl, hydroxy, oxo, aryl or heterocyclic group and at least one of carbon atom in the aliphatic hydrocarbon is optionally substituted by oxygen, nitrogen or sulfur; and
Ra is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic group or hetrocyclic-oxy group; cyclo(lower)alkyl; cyclo(lower)alkyloxy; aryl; aryloxy; heterocyclic group; heterocyclic-oxy group.

A group of particularly preferable compounds among the above-described compounds is represented by the formula (II):

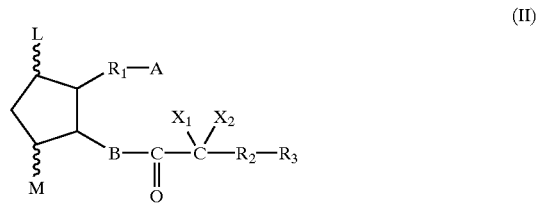

(II)

wherein L and M are hydrogen, hydroxy, halogen, lower alkyl, hydroxy(lower)alkyl or oxo, wherein at least one of L and M is a group other than hydrogen, and the five-membered ring may have at least one double bond;
A is —CH$_2$OH, —COCH$_2$OH, —COOH or a functional derivative thereof;
B is —CH$_2$—CH$_2$—, —CH=CH—, —C≡C—;
X$_1$ and X$_2$ are hydrogen, lower alkyl, or halogen;
R$_1$ is a saturated or unsaturated bivalent lower or medium aliphatic hydrocarbon residue, which is unsubstituted or substituted with halogen, alkyl, hydroxy, oxo, aryl or heterocyclic group and at least one of carbon atom in the aliphatic hydrocarbon is optionally substituted by oxygen, nitrogen or sulfur;
R$_2$ is a single bond or lower alkylene; and
R$_3$ is lower alkyl, lower alkoxy, cyclo(lower)alkyl, cyclo(lower)alkyloxy, aryl, aryloxy, heterocyclic group or heterocyclic-oxy group.

In the above formula, the term "unsaturated" in the definitions for R$_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 6 to 10 carbon atoms for R$_1$ and 1 to 10, especially 1 to 8 carbon atoms for R$_a$.

The term "halogen" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O-, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O-, wherein cyclo(lower)alkyl is as defined above.

The term "aryl" may include unsubstituted or substituted aromatic hydrocarbon rings (preferably monocyclic groups), for example, phenyl, tolyl, and xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tri-cyclic, preferably monocyclic heterocyclic group which is 5 to 14, preferably 5 to 10 membered ring having optionally substituted carbon atom and 1 to 4, preferably 1 to 3 of 1 or 2 types of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolonyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino) ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base, or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A means a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonyl-amide and tolylsulfonylamide.

Preferred examples of L and M include hydroxy and oxo, and especially, M is hydroxy and L is oxo which has a 5-membered ring structure of, so called, PGE type.

Preferred example of A is —COOH, its pharmaceutically acceptable salt, ester or amide thereof.

Preferred example of B is —CH$_2$—CH$_2$—, which provide the structure of so-called, 13,14-dihydro type.

Preferred example of X$_1$ and X$_2$ is that at least one of them is halogen, more preferably, both of them are halogen, especially, fluorine that provides a structure of, so called 16,16-difluoro type.

Preferred R$_1$ is a hydrocarbon containing 1–10 carbon atoms, preferably, 6–10 carbon atoms. Further, at least one of carbon atom in the aliphatic hydrocarbon is optionally substituted by oxygen, nitrogen or sulfur.

Examples of R$_1$ include, for example, the following groups:

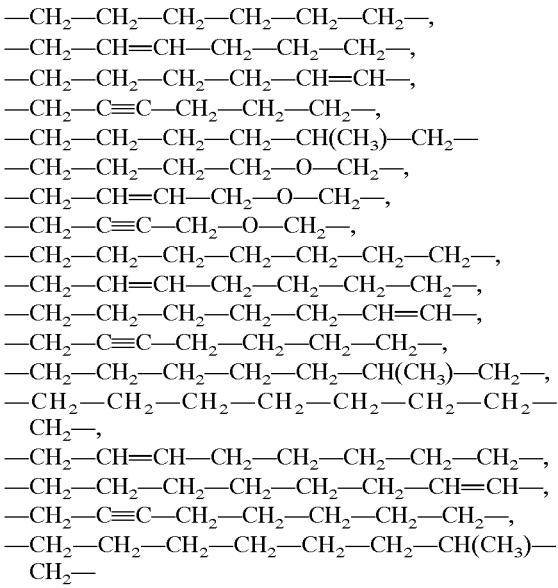

Preferred Ra is a hydrocarbon containing 1–10 carbon atoms, more preferably, 1–8 carbon atoms. Ra may have one or two side chains having one carbon atom.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

The Examples of the typical compound in the invention are 13,14-dihydro-15-keto-16-mono or difluoro-PGE compound, the derivatives or analogs thereof.

The 15-keto-PG compound of the present invention may be in the keto-hemiacetal equilibrium by formation of a hemiacetal between hydroxy at position 11 and oxo at position 15.

For example, it has been revealed that when both of $X_1$ and $X_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the 15-keto-PG compounds used in the invention include both isomers.

Further, the 15-keto-PG compounds used in the invention include the bicyclic compound and analogs or derivatives thereof. The bicyclic compounds is represented by the formula (III)

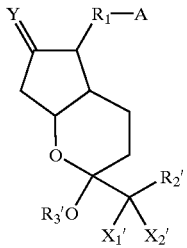

(III)

whererin, A is —CH$_2$OH, —COCH$_2$OH, —COOH or a functional derivative thereof;
$X_1'$ and $X_2'$ are hydrogen, lower alkyl, or halogen;
Y is

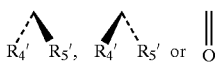

$R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.
$R_1$ is a divalent saturated or unsaturated lower or medium aliphatic hydrocarbon residue, which is unsubstituted or substituted with halogen, alkyl, hydroxy, oxo, aryl or heterocyclic group and at least one of carbon atom in the aliphatic hydrocarbon is optionally substituted by oxygen, nitrogen or sulfur; and
Ra' is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower) alkyloxy, aryl, aryloxy, heterocyclic group or hetrocyclic-oxy group; cyclo(lower)alkyl; cyclo(lower) alkyloxy; aryl; aryloxy; heterocyclic group; heterocyclic-oxy group.
$R_3'$ is hydrogen, lower alkyl, cyclo(lower)alkyl, aryl or heterocyclic group.

Further more, while the compounds used in the invention may be represented by a structure formula or name based on keto-type regardless of the presence or absence of the isomers, it is to be noted that such structure or name does not intend to exlclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324 and 5,739,161 and 6,242,485.
(these cited references are herein incorporated by reference)

The subject to be treated by the present invention may be any mammalian subject including animals and human beings. According to the method of the present invention, a pharmaceutical composition comprising a 15-keto-prostaglandin composition as an active ingredient may be administrated either systemically or topically.

Usually, the composition is administered by oral administration, intravenous injection (including infusion), subcutaneous injection, intra rectal administration, intra vaginal administration and the like. The dose of the active ingredient may vary depending on the strain i.e. particular animal or human, age, sex, body weight of the patient to be treated, symptom to be treated, desired therapeutic effect, administration route, term of treatment and the like.

Typically, a satisfactory effect can be obtained by systemic administration 1–4 times per day or continuous administration of the 15-keto-prostaglandin compound at the amount of 0.00001–100 mg/kg per day.

The composition of the present invention can be formulated as a composition for oral administration, for injection, for perfusion or for external administration, tablet, sublingual, suppository, and vaginal suppository.

The composition of the present invention may further contain physiologically acceptable additives. Said additives may include the ingredients used with the 15-keto-PG compound such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant, a functional material such as cyclodextrin and biodegradable polymer, stabilizer. The additives may be selected from those described in general reference books of pharmaceutics.

The amount of the 15-keto-prostaglandin compound contained in a composition may vary depending on the formulation of the composition, and may generally be 0.0001–10.0 wt %, more preferably 0.001–1.0 wt %.

Examples of solid compositions for oral administration include tablets, troches, sublingual tablets, capsules, pills, powders, granules and the like. The solid composition may be prepared by mixing one or more active ingredients with at least one inactive diluents. The composition may further contain additives other than the inactive diluents, for example, a lubricant, a disintegrator and a stabilizer. Tablets and pills may be coated with an enteric or gastroenteric film, if necessary. They may be covered with two or more layers.

They may also be adsorbed to a sustained release material, or microcapsulated. Additionally, the compositions may be capsulated by means of an easily degradable material such gelatin. They may be further dissolved in a appropriate solvent such as fatty acid or its mono, di or triglyceride to be a soft capsule. Sublingual tablet may be used in need of fast-acting property.

Examples of liquid compositions for oral administration include emulsions, solutions, suspensions, syrups and elixirs and the like. Said composition may further contain a conventionally used inactive diluents e.g. purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition which contains one or more active ingredients and may be prepared according to a known method.

Example of the injectable compositions of the present invention for parenteral administration include sterile aqueous or nonaqueous solutions, suspensions and emulsions comprising one or more active ingredient. Diluents for the aqueous solution or suspension may include, for example, distilled water for injection, physiological saline and Ringer's solution. Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

Another formulation of the composition according to the present invention may be rectal or vaginal suppository. Said suppository may be prepared by mixing at least one active compound according to the present invention with a suppository base e.g. cacao butter and may optionally be admixed with a nonionic surfactant having a suitable softening temperature to improve absorption.

The term "treatment" or "treating" used herein includes any means of control such as prevention, care, relief of the condition, attenuation of the condition and arrest of progression.

The term "drug-induced constipation" used herein is not limited to a particular constipation condition so far as the condition is caused by using a drug as its side effect, which also includes secondary constipation due to the drug use. Further, constipation caused by an additive or synergistic effect due to combined drug administration is also included.

Drugs which cause drug-induced constipation to be treated by the present invention may include, for example, opioids of narcotic drugs such as morphine (such as morphine hydrocholoride and MS contin) and codeine (such as codeine phosphate); anticholineric agents such as antiparkinsonism drugs (trihexyphenidyl and levodopa), antidepressants (tricyclic antidepressants such as amoxapine, trimipramine, aminotriptyline, imipramine, clomipramine, dosulepin, nortriptyline and lofepramine, tetracyclic antidepressants such as setiptiline, maprotiline and mianserin) and anti-incontinence agents (such as propanetheline and oxybutynin); antacids (such as alminium preparation), bone weight increasing agents (such as calcium preparations), diuretic, iron preparations, calcium antagonist, benzodiazepine drugs, phenothiazine drugs (such as chlorpromazine), $H_2$-blockers, pill, tocopherol. Especially, constipation conditions induced by opioid such as morphine and codeine, and antidepressants such as tricyclic antidepressants including imipramine are effectively treated 0with the composition of the present invention.

In the present invention, "a subject suffering from drug-induced constipation or a subject having a strong possibility of suffering from it" includes both a subject actually constipating due to the administration of a drug which causes constipation and a subject having a strong possibility of constipating due to the administration of a drug, for example, a subject being administered with a drug such as an opioid or an antidepressant, that is known to have a strong possibility of constipation as a side effect.

In the present invention, a dosage form may include one active ingredient only or a combination of two or more active ingredients. When a combination of a plurality of active ingredients are used, their respective contents can be suitably increased or decreased in consideration of their effects and safety.

The composition of, the present invention can further include other pharmacologically active ingredients as far as they do not contradict the purpose of the present invention.

The further details of the present invention will follow with reference to test examples, which, however, are not intended to limit the present invention.

EXAMPLE 1

Antagonism to Morphine-Induced Constipation

Male ICR mice were fasted overnight in wire-bottomed cages to prevent coprophagia, and 15 mice were used for each group. Morphine hydrochloride (Takeda Chemical Industries, Ltd., Osaka Japan) was injected intraperitoneally to animals at 5 mg/kg. Immediately after the morphine-injection, 0.1 mL graphite marker (2:1 mixture of Pilot INK-30-B and 10% tragacanth mucilage) and 5 mL/Kg vehicle (physiological saline containing 0.01% polysorbate 80 and 0.5% ethanol) or 1, 10, or 100 μg/kg test substance (13,14-dihydro-15-keto-16,16-difluoro-$PGE_1$) in 5 mL/Kg of the vehicle were administered orally. A normal control group received graphite marker and vehicle orally in the above volumes without the morphine-injection. One hundred and fifty minutes after the administration of graphite marker, animals were sacrificed by cervical dislocation, and examined the caecum for the presence of graphite marker. It was judged as a positive response when graphite marker was found in the caecum (positive score).

The number of animals in which graphite marker was found in the caecum (number of animals with positive scores) and its ratio in each group are shown in Table 1.

TABLE 1

| Group | Number of animals with positive scores[a]/ Number of animals tested | Ratio of animals with positive scores |
|---|---|---|
| Normal (vehicle) | 15/15** | 100% |
| Morphine + vehicle | 3/15 | 20% |
| Morphine + test substance | | |
| 1 μg/kg | 9/15* | 60% |
| 10 μg/kg | 13/15** | 87% |
| 100 μg/kg | 14/15** | 93% |

[a]Positive score: Presence of graphite marker in the caecum
*$p < 0.05$,
**$p < 0.01$ compared with morphine + vehicle group ($\chi^2$ test)

In the normal group, graphite marker was found in the caecum in all the 15 animals (100%).

In the morphine+vehicle group, graphite marker was found in the caecum in 3 out of 15 animals (20%). The number of positive animals in the morphine+vehicle group was significantly decreased as compared with that of the normal group, which indicated that constipation was induced by the morphine treatment.

In the groups received test substance at 1, 10 or 100 µg/kg immediately after the morphine administration, graphite marker was found dose-dependently in the caecum in 9 (60%), 13 (87%) and 14 (93%) out of 15 animals, respectively. The test substance group significantly antagonized the morphine-induced constipation as compared with control (morphine+vehicle) group.

Above results demonstrate that the substances of the present invention antagonize the opioid-induced constipation even at a low dose of 1 µg/kg.

EXAMPLE 2 (COMPARATIVE EXAMPLE)
Antagonism to Morphine-Induced Constipation

The effects of conventional cathartics (sennoside and sodium picosulfate) clinically used for the treatment of constipation in the patients applied with morphine on morphine-induced constipation were evaluated.

Sennoside (tablets: Novartis Pharma K.K., Tokyo, Japan) were crushed with mortar and ground into fine powder, and suspended in 0.5% tragacanth solution to yield proper concentration for the intended dose level of administration. Sodium picosulfate (liquid: Teijin K.K., Tokyo, Japan) was diluted with physiological saline solution.

Dosage levels of each test substance were set at 1 and 10 times of clinical daily dosage (clinical daily dosage: sennoside 24 mg, sodium picosulfate 7.5 mg; assuming body weight is 50 kg, they are equivalent to 0.48 mg/kg and 0.15 mg/kg, respectively). Each diluent for test substance was used as a vehicle.

The experimental procedure was the same as described in example 1.

The number of animals in which graphite marker was found in the caecum (number of animals with positive scores) and its ratio in each group are shown in Table 2 (sennoside) and Table 3 (sodium picosulfate).

TABLE 2

| Group | Number of animals with positive scores[a]/ Number of animals tested | Ratio of animals with positive scores |
| --- | --- | --- |
| Normal (vehicle) | 10/10** | 100% |
| Morphine + vehicle | 2/10 | 20% |
| Morphine + sennoside | | |
| 0.48 mg/kg | 2/10 | 20% |
| 4.8 mg/kg | 2/10 | 20% |

[a]Positive score: Presence of graphite marker in the caecum
**p < 0.01 compared with morphine + vehicle group ($\chi^2$ test)

TABLE 3

| Group | Number of animals with positive scores[a]/ Number of animals tested | Ratio of animals with positive scores |
| --- | --- | --- |
| Normal (vehicle) | 8/10* | 80% |
| Morphine + vehicle | 3/10 | 30% |
| Morphine + sodium picosulfate | | |
| 0.15 mg/kg | 3/10 | 30% |
| 1.5 mg/kg | 4/10 | 40% |

[a]Positive score: Presence of graphite marker in the caecum
*p < 0.05 compared with morphine + vehicle group ($\chi^2$ test)

The cathartics (sennoside and sodium picosulfate) conventionally used for the treatment of constipation in patients applied with morphine had no effect on morphine-induced constipation at the clinical daily dosage and even at 10 times of the clinical daily dosage.

Above results demonstrate that conventional cathartics, which have purgative action, does not necessarily antagonize opioid-induced constipation, and suggests that the conventional cathartics are hard to control constipation sufficiently.

EXAMPLE 3

Effect on Analgesic Action

Male ICR mice were fasted overnight in wire-bottomed cages to prevent coprophagia. The tail of the animal was pinched with clamp forceps, and the response time from the tail-pinch to fierce striking, biting or crying was measured. 18 mice whose response time of 2 second or shorter were used as test animals. Morphine hydrochloride (Takeda Chemical Industries, Ltd., Osaka, Japan) was injected intraperitoneally to the animals at 5 mg/kg. Immediately after the morphine-injection, vehicle (physiological saline containing 0.01% polysorbate 80 and 0.5% ethanol) or 1, 10, or 100 µg/kg test substance (13,14-dihydro-15-keto-16,16-difluoro-$PGE_1$) dissolved in the vehicle was administered orally in an administration volume of 5 mL/kg. The animals of normal control group received vehicle orally in the above volume without morphine-injection.

The response time of each animal following tail-pinch was measured 30, 60, 90, 120 and 150 minutes after the administration. If a mouse took longer than 10 seconds to respond, measurement was stopped to avoid injuring the tail tissue, and the response time was recorded as 10 second. Results are shown in Table 4.

TABLE 4

| Group | Number of animals | Response time, mean ± S.E., sec. | | | | | |
|---|---|---|---|---|---|---|---|
| | | Before administration | Time after administration | | | | |
| | | | 30 min | 60 min | 90 min | 120 min | 150 min |
| Normal (vehicle) | 18 | 0.9 ± 0.1 | 1.0 ± 0.1 | 1.1 ± 0.1 | 1.1 ± 0.1 | 1.1 ± 0.1 | 1.3 ± 0.1 |
| Morphine + vehicle | 18 | 1.0 ± 0.1 | 2.8 ± 0.6** | 1.9 ± 0.3* | 1.8 ± 0.4+ | 1.4 ± 0.2 | 1.2 ± 0.1 |
| Morphine + test substance | | | | | | | |
| 1 μg/kg | 18 | 1.0 ± 0.1 | 3.2 ± 0.7** | 2.3 ± 0.6+ | 1.5 ± 0.2* | 1.3 ± 0.1 | 1.3 ± 0.1 |
| 10 μg/kg | 18 | 1.0 ± 0.1 | 3.4 ± 0.5** | 1.8 ± 0.2** | 1.4 ± 0.1* | 1.3 ± 0.1 | 1.2 ± 0.1 |
| 100 μg/kg | 18 | 1.0 ± 0.1 | 2.9 ± 0.6** | 1.8 ± 0.3* | 1.5 ± 0.1* | 1.2 ± 0.1 | 1.3 ± 0.1 |

+ $p < 0.1$,
* $p < 0.05$,
** $p < 0.01$ compared with normal group (Student's t-test)
No significant difference between Morphine + vehicle group and each Morphine + test substance group (Student's t-test)

The response times before the administration were about 1 second in all the groups, and no difference was found among the groups.

In the normal group, the response time at every measurement time after the vehicle administration was not different from that of before the administration.

In the morphine+vehicle group, a significant increase in the response time was found 30 and 60 minutes after the morphine-treatment as compared with that of the normal group. The tendency for the increase of the response time was still found 90 minutes after the morphine-treatment. The analgesic effect of morphine was almost completely disappeared 120 and 150 minutes after the morphine-treatment.

In each morphine+test substance group, significant increase of response time was observed as compared with that of the normal group. In the morphine+test substance groups, the response times were similar to those observed in the morphine+vehicle group.

No significant difference in the response time was found between the morphine+vehicle group and the morphine+test substance groups, which indicates that test substance did not affect the analgesic action of morphine.

Above results demonstrates that the substances of the present invention does not affect the analgesic action of opioid even at a high dose of 100 μg/kg.

EXAMPLE 4
Antagonism to Imipramine (A Tricyclic Antidepressant)-Induced Constipation Male ICR mice were fasted overnight in wire-bottomed cages to prevent coprophagia, and 10 mice were used for each group. Imipramine hydrochloride (Wako Pure Chemical Industries, Ltd., Osaka, Japan) at 60 mg/kg was injected intraperitoneally to the animals. Immediately after the imipramine-injection, 0.1 mL of carbon marker (10% carbon powder suspension in 5% gum Arabic) and vehicle (physiological saline solution containing 0.01% polysorbate 80 and 0.5% ethanol) or test substance (13,14-dihydro-15-keto-16,16-difluoro-$PGE_1$) in an administration volume of 5 mL/kg were orally administered. A normal control group received carbon marker and vehicle in the above volume orally without the imipramine-injection. One hundred and fifty minutes after the administration of carbon marker, animals were sacrificed by cervical dislocation, and examined the caecum for the presence of carbon marker. It was judged as a positive response when carbon marker was found in the caecum (positive scores).

The number of animals in which carbon marker was found in the caecum (number of animals with positive scores) and its ratio in each group are shown in Table 5.

These results demonstrate that the substance of the present invention antagonize the imipramine-induced constipation.

TABLE 5

| Group | Number of animals with positive scores[a]/ Number of animals tested | Ratio of animals with positive scores |
|---|---|---|
| Normal (vehicle) | 9/10** | 90% |
| Imipramine + vehicle | 1/10 | 10% |
| Imipramine + test substance 10 μg/kg | 3/10 | 30% |
| Imipramine + test substance 100 μg/kg | 7/10** | 70% |

[a] Positive score: Presence of carbon marker in the caecum
**$P < 0.01$ compared with imipramine + vehicle group ($\chi^2$ test)

EXAMPLE 5 (COMPARATIVE EXAMPLE)

Antagonism to Imipramine (A Tricyclic Antidepressant)-Induced Constipation

The effect to the imipramine-induced constipation was evaluated on the cathartic (sennoside) clinically used for the treatment of the constipation in patients. Preparation and dose levels of sennoside were the same as described in example 2. The experimental procedure was the same as described in example 4.

The number of animals in which carbon marker was found in the caecum (number of animals with positive scores) and its ratio in each group are shown in Table 6.

These results demonstrate that sennoside has no effect on the imipramine-induced constipation.

TABLE 6

| Group | Number of animals with positive scores[a]/ Number of animals tested | Ratio of animals with positive scores |
|---|---|---|
| Normal (vehicle) | 7/10** | 70% |
| Imipramine + vehicle | 1/10 | 10% |
| Imipramine + sennoside 0.48 μg/kg | 2/10 | 20% |

TABLE 6-continued

| Group | Number of animals with positive scores[a]/ Number of animals tested | Ratio of animals with positive scores |
|---|---|---|
| Imipramine + sennoside 4.8 μg/kg | 2/10 | 20% |

[a]Positive score: Presence of carbon marker in the caecum
**P < 0.01 compared with imipramine + vehicle group ($\chi^2$ test)

What is claimed is:

1. A method for treating drug-induced constipation comprising a step of administering an effective amount of 15-keto-prostaglandin compound to a subject suffering from drug-induced constipation or in need thereof of such treatment, wherein the 15-keto-prostaglandin compound is one represented by formula (I):

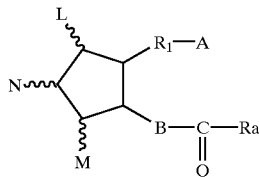

(I)

wherein

L,M and N are hydrogen, hydroxy, halogen, lower alkyl, hydroxy(lower)alkyl or oxo, wherein at least one of L and M is a group other than hydrogen, and the five-membered ring may have at least one double bond;

A is —$CH_2OH$, —$COCH_2OH$, —COOH or a functional derivative thereof;

B is —$CH_2$—$CH_2$—, —CH=CH— or —C≡C—;

$R_1$ is a saturated or unsaturated bivalent lower or medium aliphatic hydrocarbon residue, which is unsubstituted or substituted with halogen, alkyl, hydroxy, oxo, aryl or heterocyclic group and at least one carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic group or heterocyclic-oxy group; cyclo(lower)alkyl; cyclo(lower)alkyloxy; aryl; aryloxy; heterocyclic group; heterocyclic-oxy group.

2. The method of claim 1, wherein the 15-keto-prostaglandin compound is a 13,14-dihydro-15-keto-prostaglandin compound.

3. The method of claim 1, wherein the 15-keto-prostaglandin compound is a 15-keto-16-mono- or di-halogen-prostaglandin compound.

4. The method of claim 1, wherein the 15-keto-prostaglandin compound is a 13,14-dihydro-15-keto-16-mono- or di-halogen-prostaglandin compound.

5. The method of claim 2, wherein the 15-keto-prostaglandin compound is a 15-keto-16-mono- or di-fluoro-prostaglandin compound.

6. The method of claim 2, wherein the 15-keto prostaglandin compound is a 13,14-dihydro-15-keto-16-mono- or di-fluoro-prostaglandin compound.

7. The method of claim 2, wherein the 15-keto-prostaglandin compound is a 15-keto-prostaglandin E compound.

8. The method of claim 2, wherein the 15-keto-prostaglandin compound is 13,14-dihydro-15-keto-16,16-difluoro-prostaglandin $E_1$.

9. The method of claim 2, wherein the drug inducing constipation is an opioid compound.

10. The method of claim 9, wherein the opioid compound is a morphine compound or a codeine compound.

11. The method of claim 1, wherein the drug inducing constipation is an anticholinergic drug.

12. The method of claim 11, wherein the anticholinergic drug is a tricyclic antidepressant.

* * * * *

UNITED STATES PATENT AND TRADEMARK OFFICE
CERTIFICATE OF CORRECTION

| | |
|---|---|
| PATENT NO. | : 6,982,283 B2 |
| APPLICATION NO. | : 10/135397 |
| DATED | : January 3, 2006 |
| INVENTOR(S) | : Ryuji Ueno |

It is certified that error appears in the above-identified patent and that said Letters Patent is hereby corrected as shown below:

On the cover page of the patent, under "(56) References Cited", please include the following references considered by the Examiner:

For "U.S. PATENT DOCUMENTS", please insert the following:

| | | |
|---|---|---|
| 4,158,062 | 6/1979 | Caton et al. |
| 5,164,415 A | 11/1992 | Ueno |

For "FOREIGN PATENT DOCUMENTS", please insert the following:

| | | |
|---|---|---|
| EP | 0 310 305 A2 | 4/1989 |
| EP | 0 424 156 A2 | 4/1991 |
| JP | 2-32055 A | 2/1990 |

For "OTHER PUBLICATIONS", please insert the following:

Dajani, E.Z. II et al., "Effects of E Prostaglandins, Diphenoxylate and Morphine on Intestinal Motility In Vivo", European Journal of Pharmacology, Vol. 34, No. 1, 1975, pages 105-113

Signed and Sealed this

Sixth Day of February, 2007

JON W. DUDAS
*Director of the United States Patent and Trademark Office*